United States Patent [19]

Conners

[11] 4,407,069

[45] Oct. 4, 1983

[54] SCISSORS WITH CUSHIONED STOP

[75] Inventor: John A. Conners, Fairfield, Conn.

[73] Assignee: The Scott & Fetzer Company, Shelton, Conn.

[21] Appl. No.: 328,651

[22] Filed: Dec. 8, 1981

[51] Int. Cl.³ .............................................. B26B 13/20
[52] U.S. Cl. .......................................... 30/254; 30/271
[58] Field of Search .......................... 30/271, 254, 341

[56] References Cited

U.S. PATENT DOCUMENTS

| D. 198,963 | 8/1964 | Ericson | 30/254 X |
|---|---|---|---|
| 2,059,074 | 10/1936 | Whyte | 30/271 |
| 2,965,967 | 12/1960 | Wahl | 30/254 X |
| 3,846,910 | 11/1974 | Davis | 30/271 |
| 3,894,336 | 7/1975 | Desimone | 30/341 |
| 4,150,484 | 4/1979 | Hildebrandt | 30/254 |

FOREIGN PATENT DOCUMENTS 199932  7/1923  United Kingdom ................. 30/271

*Primary Examiner*—Jimmy C. Peters
*Attorney, Agent, or Firm*—Pearne, Gordon, Sessions, McCoy, Granger & Tilberry

[57] ABSTRACT

First and second metal blades made from uniform thickness stock are fashioned into scissors which may be disposable suture scissors. Each of the blades is stamped from sheet metal, they are pivoted together, and handles extend in the opposite direction from cutting edges on the blades. Resilient means is provided by the handles being resilient and stop means are provided to limit the closed position of the cutting edges to prevent overriding, namely overclosing, of the cutting edges. The stop means includes first and second stop surfaces integral with the first and second blades, respectively. The stop surfaces are close to the pivot relative to the length of the handles, the blades have only frictional opposition to movement until the stop surfaces engage, and then the subsequent stressing of the resilient means establishes a cushioned stop of movement of the handles without any further movement of the cutting edges past the fully closed condition. The foregoing abstract is merely a resume of one general application, is not a complete discussion of all principles of operation or applications, and is not to be construed as a limitation on the scope of the claimed subject matter.

13 Claims, 8 Drawing Figures

U.S. Patent   Oct. 4, 1983   4,407,069
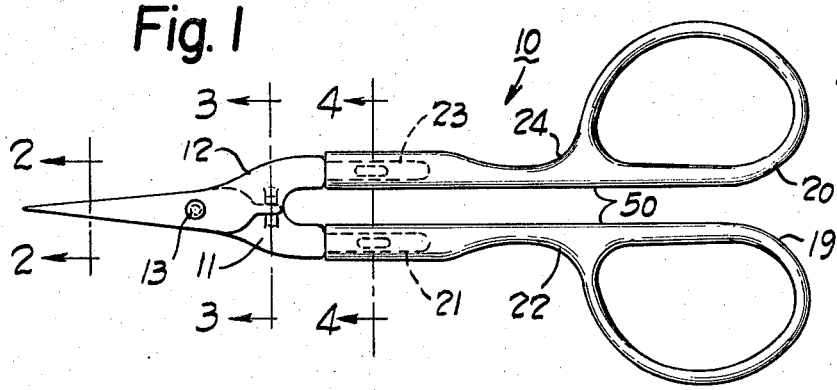
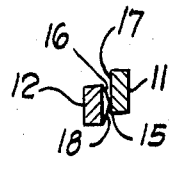
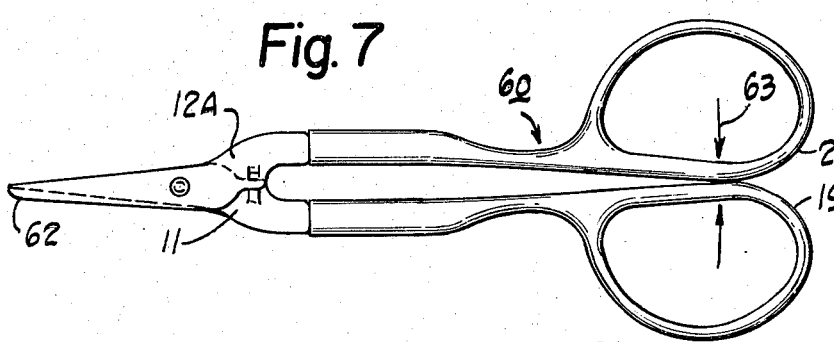
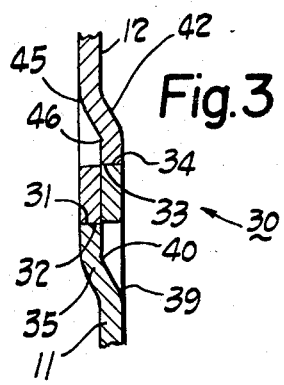
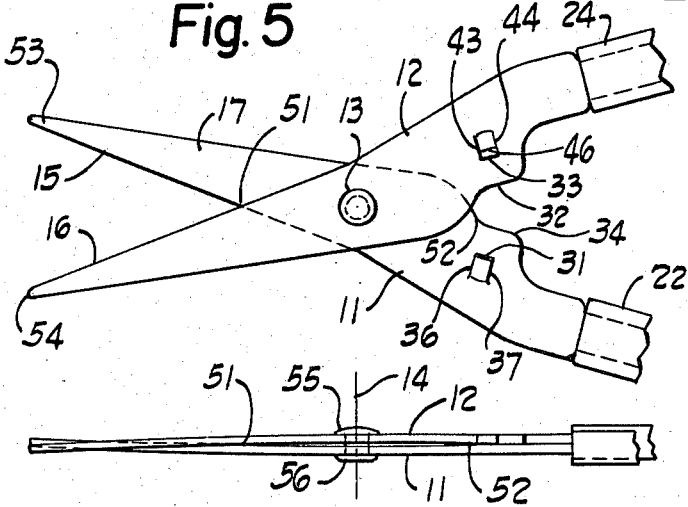
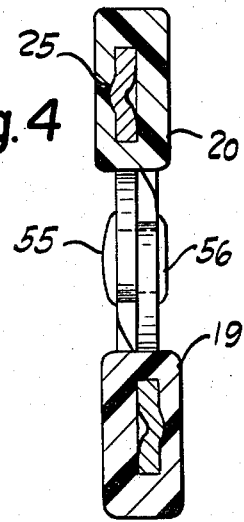
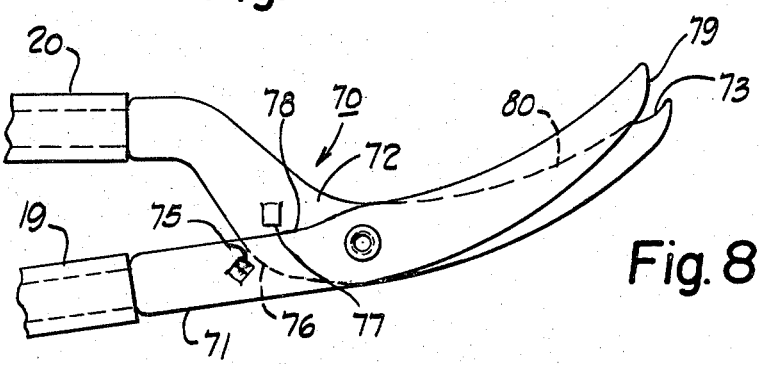

SCISSORS WITH CUSHIONED STOP

BACKGROUND OF THE INVENTION

The invention is particularly adapted to scissors which are economical to manufacture and assemble into a completely operable unit without overriding or overrunning of the material trapped between the blades. One specific use for such scissors is as disposable suture scissors, often desired by a physician because they are ready for use without necessity for fresh sterilization and they will cut cleanly at the very tip of the cutting edges, yet are sufficiently economical to be disposable without the necessity for subsequent cleaning and sterilization before reuse.

It has been necessary to sterilize surgical instruments in hospitals and doctors' offices, and this has become increasingly costly in both time and personnel involved. Accordingly, this has emphasized the great desirability for surgical instruments that may be sterilized at the plant of the manufacturer and sterile-packaged, and which may then be removed from the sterile package, used, and disposed of immediately after use. This eliminates the clean-up and subsequent sterilization, and also eliminates the delay for sterilizing the instrument before it may be used.

The prior art has known a previous attempt to make a disposable suture cutter, as set forth in U.S. Pat. No. 3,003,236. Such suture cutter was formed from a single strip of stainless steel, bent and twisted, and interengaged at a unitary pivot so as to act as a cutter. Due to the construction, which included the single strip of metal which formed the cutter and interconnected handles, the cutter was continuously biased open so that there was no protection for the cutting edges. Also, the unitary pivot strut from the metal of one blade established a poor pivot connection, with inherent lost motion. The cutter was provided with a stop, but it was a piece of metal bent from one edge of one blade and disposed at about a 45-degree angle to the plane of the blade so that there was a sharp edge on the stop extending beyond the thickness of the cutter, which could scratch a person on which the sutures were being cut, and also, due to the angular disposition of the stop, the handles could be latched closed. Further, due to the angular disposition of the stop, the blades could be forced together at the rear of the pivot, which would tend to separate the blades transversely at the cutting edges, impairing the cutting action.

A still further objection is that, due to the one-piece construction, the handles were normally disposed in a condition in which the cutting edges were biased open so that there was no protection for the cutting edges. Then, in order to utilize the cutter, the operator had to squeeze the handles together, and the more they were squeezed together, the more force was required to overcome the inherent spring bias of such handles. This relatively high closing force meant that once the stop was engaged, the operator could hardly tell that such stop had been engaged because there was little added resistance to movement of the handles, and hence the operator tended to overclose the handles because there was not a good "feel" or tactile sensation of the stop means actually interengaging.

The problem to be solved, therefore, is how to construct scissors which may be economically manufactured and assembled for proper operation, wherein the scissors may have a properly positioned stop for preventing overclosing of the cutting edges, with the stop having a positive action which is cushioned.

SUMMARY OF THE INVENTION

This problem is solved by scissors comprising, in combination, first and second blades made from flat stock of substantially uniform thickness and each having a cutting edge and an inner side surface, pivot means acting between said blades and establishing a pivot axis for the blades for cutting cooperation of said cutting edges by sliding past one another substantially parallel to said inner side surfaces, a handle on the end of each blade opposite the respective cutting edge, stop means establishing the closed position of the scissors, said stop means including a first stop surface integral with said first blade, a second stop surface integral with said second blade, each of said stop surfaces and said entire stop means lying within the thickness of said two blades, resilient means including at least one of said handles or said stop means being resilient, said first and second stop surfaces being located close to said pivot axis relative to the length of said handles to establish substantially face-to-face abutment therebetween with the cutting edges closed but with the handles still slightly spaced apart and with each cutting edge protected by said inner side surface of the other blade, and the blades presenting minimal opposition to movement of said handles until said stop surfaces engage and then the subsequent stressing of said resilient means establishing a cushioned stop of movement of said handles.

An object of the invention, accordingly, is to construct scissors with cutting edges on two blades and with a cushioned stop.

Another object of the invention is to provide scissors made from flat metal stock of substantially uniform thickness which scissors have a positive stop to prevent overrunning and overriding, yet the stop movement of the handles is not nearly as abrupt as the stopping action of the cutting edges.

Other objects and a fuller understanding of the invention may be had by referring to the following description and claims, taken in conjunction with the accompanying drawings.

BRIEF DESCRIPTION OF THE DRAWINGS

FIG. 1 is a plan view of sharp pointed scissors embodying the invention;

FIG. 2 is an enlarged, sectional view on line 2—2 of FIG. 1;

FIG. 3 is an enlarged, sectional view on the line 3—3 of FIG. 1;

FIG. 4 is an enlarged, sectional view on the line 4—4 of FIG. 1;

FIG. 5 is an enlarged, partial plan view of the scissors of FIG. 1 in an open position;

FIG. 6 is a front view of the scissors of FIG. 5;

FIG. 7 is a plan view of a modification with the handles forced together; and

FIG. 8 is an enlarged, partial, plan view of the other side of a second modified form of scissors.

DESCRIPTION OF THE PREFERRED EMBODIMENTS

FIGS. 1 through 6 illustrate scissors 10 which embody the invention, and in general these scissors include first and second blades 11 and 12, respectively. Pivot means 13 acts between the two blades and establishes a pivot axis 14 for the blades for cutting cooperation of cutting edges 15 and 16 on the blades 11 and 12, respectively. These cutting edges 15 and 16 perform a cutting operation by sliding past one another substantially parallel to inner side surfaces 17 and 18 on the first and second blades, respectively. First and second handles 19 and 20 are provided on the end of each blade opposite its respective cutting edge 15 and 16 in order to manipulate the scissors 10. In this preferred embodiment, the handles are composite handles, partially of metal and partially of a reinforced plastic. The metal portion of the handle is a first portion 21 unitary with the first blade 11, and the second handle portion 22 is a separate piece secured to this first handle portion 21. In the embodiment of FIG. 1, the first blade 11 and the first handle portion 21 are unitary and made from metal stock of substantially uniform thickness, e.g., stainless steel. The second handle portion 22 is a hardened plastic, and one suitable material which has been used is a nylon material which has been filled 40% with glass fibers. The second blade 12 also has a composite handle with a first handle portion 23 unitary with the blade 12 and a second handle portion 24 of plastic. The plastic handle-portions 22 and 24 are molded separately from the first handle-portions 21 and 23, and then pushed onto the first handle-portions 21 and 23. To help secure them together, a lug 25 is pressed into the first handle-portions 21 and 23 in order to create extra frictional resistance to insertion or removal of the first handle-portions.

Stop means 30 is provided to establish the closed position of the scissors 10. This stop means includes a first stop surface 31 integral with the first blade 11 and cooperable with a second stop surface 32 integral with the second blade 12. In this preferred embodiment, the stop means also includes a third stop surface 33 integral with the second blade 12, and cooperable with a fourth stop surface 34 integral with the first blade 11. The first stop surface 31 in this embodiment is not only integral but unitary with the first blade 11, and is formed by a first lug 35 lanced from the material of the first blade 11. This first lug 35 has three surfaces 36, 31, and 37, respectively, sheared from the metal blade 11 in a generally U-shape and displaced approximately the full thickness of the blades so that the first surface 31 is displaced entirely out of the thickness of the blade 11. The lug 35 has a first bend 39 to bend the lug away from the general plane of the first blade 11, and then a second bend 40 in a reverse direction so that the first stop surface 31 is substantially perpendicular to the plane of the blade 11. The second stop surface 32 is on the edge of blade 12 and is also substantially perpendicular to the plane of the blade so that these first and second stop surfaces 31 and 32 will abut when the scissors are in the closed position as shown in FIG. 1.

The third stop surface 33 is similarly constructed. A second lug 42 is lanced from the material of the second blade 12 and this lanced lug has surfaces 43, 33, and 44 disposed generally in a U-shape, with the third surface 33 being on the base of this U-shape as the stop surface. The second lug 42 has a first bend 45 to bend the lug out of the plane of the second blade 12 and has a second bend 46 in a reverse direction so that the stop surface 33 is substantially perpendicular to the plane of the blade 12. The fourth stop surface 34 is on the edge of blade 11 and is also substantially perpendicular to the plane of the blade 11 so that these two stop surfaces are in face-to-face abutment when the scissors 11 are closed. In this preferred embodiment, the lug 42 has the two bends 45 and 46 so that the third stop surface 33 is substantially out of the thickness of the second blade 12, yet the entire stop means 31-34 is substantially within the thickness of the entire scissors 10.

Resilient means 50 is provided in the scissors and it includes at least one of the handles 19 and 20, or the stop means 30 being resilient. In this preferred embodiment, both of the handles 19 and 20 are resilient by being made from a reinforced plastic. As stated above, one satisfactory material is the 40% glass-filled nylon, and these are autoclavable at 272° F., so that the scissors 11 may be used as surgical instruments to be sterilizable and reusable. Alternatively, the surgical scissors usage may be scissors which are disposable because the present design is sufficiently economical to permit total economy of use, which would include purchase and one use followed by disposal instead of purchase and use plus cleaning and sterilizing in order to be reused.

FIGS. 5 and 6 illustrate the scissors 10 in the open position to better illustrate the stop surfaces 31-34. FIG. 6 illustrates that the two blades 11 and 12 are bowed transversely relative to each other, and either one or both blades may be slightly bowed. Such bow of one or both blades establishes a first touching point 51 between the cutting edges 15 and 16, which touching point travels from near the pivot toward the tips 53 and 54 of the blades 11 and 12, respectively as the scissors are closed. A second touching point 52 is to the rear of the pivot means 13 which, in this preferred embodiment, is established by a rivet having a manufactured head 55 and a peened head 56. The rivet 13 preferably is a close fit but not an interference fit in the apertures in the blades 11 and 12 so that the scissors blades may swing freely with only minimal opposition to movement of the blades until the stop surfaces engage. This minimal opposition to movement is established by the slight friction at the pivot and at the touching points 51 and 52. In one scissors constructed in accordance with the invention, this minimal opposition to movement was only about two ounces of force applied at the handles 19 and 20 to cause the scissors to close. After closing, and upon engagement of the stop means 30, it required about 22-24 ounces of force applied at the handles, as shown by the force arrows 63 on FIG. 7, to force the handles together. This is considerably overstressing, and establishes the cushioned stop of the handles after the blade cutting edges have stopped moving by the engagement of the stop means 30. The cutting, especially in surgical suture scissors, is done almost always at the very tips 53 and 54, and the scissors of the preferred embodiment do provide this cutting action completely to the tip of the cutting edges. This is controlled by the precise position of the stop means so that the cutting edges close completely to the tip but do not overclose, which can cause lateral tearing of the material being cut.

FIG. 7 illustrates a modification of the invention in scissors 60, which include one sharp tip blade 11 and a modified blade 12A with a blunt tip 62. In other respects, these scissors 60 may be the same as the scissors 10 of FIGS. 1-6.

FIG. 8 illustrates a third embodiment of the invention with curved surgical scissors 70. These scissors include a first curved blade 71, which would be a top blade, and a second curved blade 72, which is a bottom blade. This bottom blade includes a Spencer tip 73, namely a small arcuate indentation in the cutting edge, to aid cutting at the very tips of the blades 71 and 72. The stop means in the scissors 70 are formed by a first stop surface 75 on the first blade 71, which is cooperable with a second stop surface 76 on the edge of the bottom blade 72. Also, this stop means includes a third stop surface 77 on the bottom blade 72 cooperable with a fourth stop surface 78 on the upper edge of the top blade 71. In a manner similar to that shown in FIG. 3, the stop surfaces 75 and 77 are formed by one sheared side surface of a U-shaped lanced lug, as in the scissors 10 and 60. When the first and second stop surfaces 75 and 76 abut each other in face-to-face engagement, similarly to that shown in FIG. 3, and also the third and fourth stop surfaces 77 and 78 are in engagement, within the limits of tolerance of manufacture, the handles 19 and 20 will be substantially parallel to each other, as shown in FIG. 1, and they will be spaced apart, e.g., one-quarter inch, at the time the stop surfaces come into abutment. Again, the handles are resilient to establish a cushioned stop to the handle movement even though the cutting edges 79 and 80 are held stationary by the stop means 75–78.

It will be noted that in all three of the embodiments of the invention, in the scissors 10, 60, and 70, the stop means is established by at least one shear cut in the first blade 11 or 71. The lug 35 or 42 has at least one bend to establish this stop surface out of the plane of the blade, or out of the thickness of that particular blade. Also, it will be noted that in the preferred embodiment, the lug has two bends in opposite directions so that the stop surface 31, for example, is established substantially perpendicular to the plane of the blade. In this manner, the two stop surfaces 31 and 32, for example, abut in face-to-face engagement along a plane substantially perpendicular to the plane of the blades. By this means, there is no force generated perpendicular to the plane of the blades which tends to spread the cutting edges transversely apart, which could cause overriding, namely trapping of the material to be cut between the planes of the blades.

In one embodiment actually constructed in accordance with the invention, the stop means 30 was about 0.5 inch from the pivot axis 14, whereas the finger grips on the handles 19 and 20 were about 3.5 inches from the pivot axis. Accordingly, the stop means were provided sufficiently far from the pivot axis to be able to precisely control the closed position of the cutting edges, with each cutting edge protected by the inner side surface of the other blade. Accordingly, the stop means prevents overrunning, namely overclosing, of the blades, yet establishes a cushioned stop movement for the handles 19 and 20 because of the length and resiliency of the handles relative to the position of the stop means 30. The stop means are formed by lanced lugs which may be formed by a press at the same time that the lugs 25 are formed, to retain the plastic handles 22 and 24 on the handle portions 21 and 22. These lanced lugs halt the motion of the surgical suture cutting blades at precisely the desired position. The fact that the first and second stop surfaces 31 and 32 are substantially perpendicular to the plane of the blade has two functions, the first being that it minimizes the likelihood of the blades sticking in the closed position, and the second being that it prevents the rear part of the blades from being forced together, which might exert a force transversely, tending to separate the cutting edges, which otherwise could cause overriding of the material to be cut. Also, the height of the lanced lugs 35 and 42 is chosen to be approximately the thickness of the blade, and thus the combined stop means upon closing of the scissors is approximately the same thickness as the total thickness of the scissors. By this means, the stop means does not extend excessively in a lateral direction, which would otherwise enable the stops to come into contact with the surrounding environment. The positive stop of the cutting edges and the cushioned stop of the handles prevent overrun of the two cutting edges, which could cause damage to the bow of each blade, changes in the rivet action, and misalignment of the blade handles. The use of the two pairs of stop surfaces ensures that a variety of finger pressures and motions by different users will be adequately compensated.

The placement of the stop is preferably such that the handles are spaced apart about 0.25 inch when the scissors blades are in the closed position as shown in FIG. 1. If the user ignores the definite tactile sensation of the closed position and squeezes with excessive force, then the handles can touch as shown in FIG. 7; however, this is not normal usage and merely illustrates that the handles have sufficient elastic strength to permit such stressing.

Since the handles are composite handles, partly metal and partly plastic, the economy of manufacture of the scissors is aided, so that they are economically disposable after a single use. Due to variations in manufacture and different tolerances from one batch to another, the handles 19 and 20 may not have the identical closed position from one scissors to the next. Nevertheless, the placement of the stop means 30 on the metal portion of the blades obviates the necessity for precise positioning of the plastic handles on the blade handle first portions 21 and 23.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention as hereinafter claimed.

What is claimed is:
1. Scissors comprising, in combination:
first and second blades made from flat stock of substantially uniform thickness and each having a cutting edge and an inner side surface;
pivot means acting between said blades and establishing a pivot axis for the blades for cutting cooperation of said cutting edges by sliding past one another substantially parallel to said inner side surfaces;
a handle on the end of each blade opposite the respective cutting edge;
stop means establishing the closed position of the scissors;
said stop means including a first stop surface unitary with said first blade;
a second stop surface unitary with said second blade and abuttable with said first stop surface to limit the closed position of said blades;
a third stop surface unitary with said second blade;
a fourth stop surface unitary with said first blade and abuttable with said third stop surface to limit the closed position of said blades at substantially the same time as abutment between said first and second stop surfaces;
each of said stop surfaces and said entire stop means lying within the thickness of said two blades;

said stop means including at least two shear cuts in said first blade establishing said first stop surface, and a bend in the material of said first blade between said two shear cuts to establish the blade material therebetween bent out of the thickness of said first blade and with said first stop surface at least partially out of the thickness of said first blade;

resilient means including at least one of said handles or said stop means being resilient;

said first and second stop surfaces and said third and fourth stop surfaces being located close to said pivot axis relative to the length of said handles to establish substantially face-to-face abutment therebetween with the cutting edges closed yet the handles still slightly spaced apart and with each cutting edge protected by said inner side surface of the other blade; and the blades presenting minimal opposition to movement of said handles until said stop surfaces engage and then the subsequent stressing of said resilient means establishing a cushioned stop of movement of said handles.

2. Scissors as set forth in claim 1, wherein said stop means includes a U-shaped tongue lanced from the stock of said first blade with one of the sides of said U-shaped tongue established as said first stop surface.

3. Scissors as set forth in claim 2, wherein the base of said U-shape is said first stop surface.

4. Scissors as set forth in claim 2, wherein said lanced tongue has first and second bends in opposite directions to establish said tongue in a position with said first stop surface substantially entirely out of the thickness of said first blade and yet establish said stop means substantially entirely within the thickness of the scissors.

5. Scissors as set forth in claim 1, wherein at least one of said handles is resilient.

6. Scissors as set forth in claim 1, wherein both of said handles are resilient.

7. Scissors as set forth in claim 1, wherein each of said first and second stop surfaces are substantially perpendicular to the plane of the respective blade.

8. Scissors as set forth in claim 1, wherein each of said first and third stop surfaces are formed as one edge of lanced U-shaped tongues on the respective blades.

9. Scissors as set forth in claim 1, wherein said first and second stop surfaces and said fourth and third stop surfaces are disposed at an angle to the respective first and second blades so that when said first and second stop surfaces are forced together, there is an absence of a component of force generated perpendicular to the plane of the blades in a direction which tends to move said cutting edges away from each other.

10. Scissors as set forth in claim 1, wherein at least one of said blades has a composite handle of a first portion unitary with said cutting edge and a second portion secured to said first portion, and said stop surface on said one of said blades being on said handle first portion.

11. Scissors as set forth in claim 10, wherein the length of said composite handle from said pivot axis is at least five times the distance from said pivot axis to said stop surface on said one of said blades and said handle second portion is resilient to establish said resilient means.

12. Scissors as set forth in claim 11, wherein the precise position of securing said second handle portion to said first handle portion is obviated by said stop means being on said first handle portion rather than on said second handle portion.

13. Scissors as set forth in claim 1, wherein said handles are spaced apart in the order of 0.25 inch when said stop surfaces are initially moved into closing engagement and said resilient means having sufficient resiliency to permit said handles to be forced into mutual engagement and said abutting stop surfaces still preventing overriding of said cutting edges.

* * * * *